Figure 2:
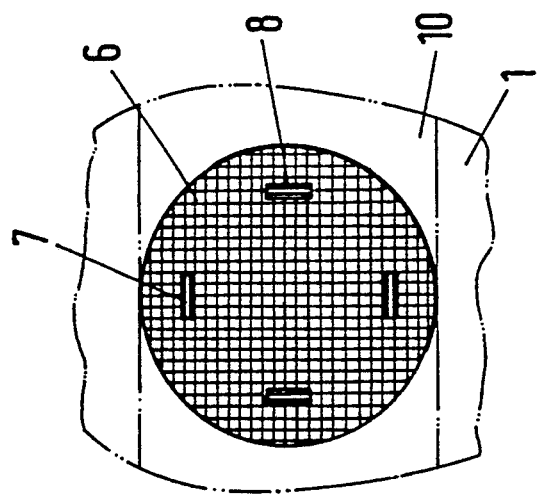

United States Patent [19]

Gschwend et al.

[11] Patent Number: 5,181,924
[45] Date of Patent: Jan. 26, 1993

[54] PATELLA PROSTHESIS

[75] Inventors: Norbert Gschwend, Zürich; Rudolf Koch, Frauenfeld, both of Switzerland

[73] Assignee: Sulzer Medizinaltechnik AG, Winterthur, Switzerland

[21] Appl. No.: 888,743

[22] Filed: May 26, 1992

[30] Foreign Application Priority Data

Jul. 5, 1991 [CH] Switzerland ............... 2004/91

[51] Int. Cl.$^5$ .............................................. A61F 2/38
[52] U.S. Cl. ............................................. 623/20; 623/18
[58] Field of Search ........................ 623/16, 18, 20

[56] References Cited

U.S. PATENT DOCUMENTS

| | | | |
|---|---|---|---|
| 4,550,448 | 11/1985 | Kenna | 623/20 X |
| 4,955,911 | 9/1990 | Frey et al. | 623/16 |
| 4,997,445 | 3/1991 | Hodorek | 623/16 |
| 5,019,104 | 5/1991 | Whiteside et al. | 623/20 |

FOREIGN PATENT DOCUMENTS

| | | |
|---|---|---|
| 0338976 | 10/1989 | European Pat. Off. |
| 0420795 | 4/1991 | European Pat. Off. |
| 2653992 | 5/1991 | France ............... 623/20 |

Primary Examiner—Ronald Frinks
Attorney, Agent, or Firm—Townsend & Townsend

[57] ABSTRACT

The invention shows a patella prosthesis, which consists of an artificial slide member (2) made from polyethylene with the slide member (2) being mounted on the rear of the patella (1) by means of an attachment. The sliding surface (3) consists of the sector of a polyethylene sphere, which comprises a metal grid (4) of an attachment member (9). The attachment member consists of a metal sandwich construction having a central support sheet and metal grids (4, 6) spot welded on both sides, with bevelled sheet metal flanges (7) for the primary attachment of the support sheet (5) protruding through recesses (8) in the metal grid (6) on the side of the patella.

2 Claims, 1 Drawing Sheet

PATELLA PROSTHESIS

The invention relates to a patella prosthesis which consists of an artificial slide member having a sliding surface which is mounted from the rear of the patella by means of an attachment.

U.S. Patent specification No. 4,479,271 shows a patella prosthesis in which the primary attachment is performed by pegs, which consist of a metal core which is surrounded by a porous fibrous shell, which in turn is placed with dimensional accuracy on the outside and on the inside of a non-metallic peg made of polyethylene. The recesses for the pegs have to be incorporated in the patella and should lie with their axes at right angles to the plane for the actual mounting surface so as to enable its abutment and subsequent fusion. The spacing and position of the location holes in the patella also have to be very precise.

The invention finds a solution to this problem. The object of the invention is to attach a patella prosthesis in the patella with only very simple preparatory work being required. This object is achieved according to the invention in that the sliding surface consists of the sector of a polyethylene sphere, which comprises a metal grid of an attachment member, and in that the attachment member consists of a metal sandwich construction having a central support sheet and metal grids spot welded on both sides, with bevelled sheet metal flanges for the primary attachment of the support sheet protruding through recesses in the metal grid on the side of the patella.

The advantages of the invention are regarded as being that only one plane supporting surface has to be created on the patella as a preparation, that the prosthesis has high inherent strength and dimensional stability and that the delimitation surface for the fusing osseous tissue is made of metal. The design of the prosthesis also produces advantages from the point of view of manufacturing engineering by an attachment part being created using purely sheet metal working methods and the slide member being attached thereto in a simple joining operation.

For the primary attachment of the prosthesis it is sufficient to manufacture a flat surface element on the rear of the patella. This may be done by a flat rasp, for example, with the exact relative position of the flat surface element having secondary importance, as the sliding surface of the prosthesis is formed from the sector of a sphere. The prosthesis is placed in the correct place by the surgeon and pressed into the patella for the primary attachment. Knife-like sheet metal flanges form a self-locking primary attachment in the osseous tissue without damaging it. The loss of osseous tissue is slight.

The invention is described below by means of an exemplified embodiment.

Figure 1:
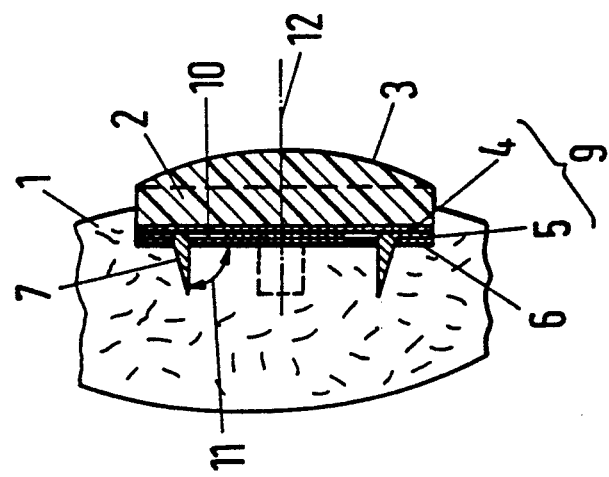

FIG. 1 shows the longitudinal section through a patella having a prosthesis as specified by the invention, and FIG. 2 shows the view of the lower side of the prosthesis close to the patella shown in FIG. 1.

In the figures is shown a patella prosthesis which consists of an artificial slide member 2 made of polyethylene with sliding surface 3, with the slide member 2 being mounted on the rear of the patella 1 by means of an attachment. The sliding surface 3 consists of the sector of a polyethylene sphere, which comprises a metal grid 4 of an attachment member 9. The attachment member consists of a metal sandwich construction having a central support sheet and metal grids 4, 6 spot welded on both sides, with bevelled sheet metal flanges 7 for the primary attachment of the support sheet protruding through recesses 8 in the metal grid 6 on the side near the patella.

FIG. 1 shows the sandwich construction of the attachment member 9, which consists of a central titanium sheet 5 having a wall thickness of 0.5 mm and grids 4, 6 made of titanium spot welded on both sides. The attachment member 9 is cut to size as a disc with a diameter of 27 mm. The slide member 2 consists of a disc having the same diameter and ends with a spherical sliding surface 3 having a radius of 30 mm and a central point in the axis 12 of the discs. The metal grid 4 on the side of the slide member 2 penetrates it and is surrounded by polyethylene right up to the support sheet 5.

In FIG. 2 the metal grid 6 on the side of the patella has four rectangular recesses 8 in the orientation of the grid, through which a bevelled sheet metal flange 4 mm wide by 6 mm protrudes from the support sheet 5. The sheet metal flanges 7 have been cut free from the support sheet 5 with a blanking die (not shown) along the protruding contour and have been bent by an angle 11 of 90° from the plane of the support sheet 5.

The attachment is made on the inside of the patella on a per se plane attachment surface 10, which was produced with a flat rasp (not shown) at right angles to the chord. The prosthesis is placed in a position on the patella 1 which is corrected by the length of the protruding sheet metal flange and pressed into its final position. The knife-like sheet metal flanges 7 become embedded in the osseous tissue and by self-locking in the displaced osseous tissue form a primary attachment for the whole prosthesis. The osseous tissue can fuse without obstruction right to the support sheet 5 through the metal grid 6 on the side of the patella. The support plate 5 is so rigid per se that forces on the contact points of the sliding surface 3 are evenly transmitted to the osseous tissue fused in the metal grid 6.

We claim:

1. A patella prosthesis comprising an artificial slide member having a sliding surface, which is adapted to be mounted on the rear of the patella by means of an attachment, the sliding surface including the sector of a polyethylene sphere, which comprises a metal grid of an attachment member formed by a metal sandwich construction having a central support sheet and metal grids spot welded on both sides, with bevelled sheet metal flanges for the primary attachment of the support sheet protruding through recesses in the metal grid for being mounted in contact with the rear of the patella.

2. A patella prosthesis according to claim 1, wherein the sheet metal flanges are a component of the support sheet and are cut free by a blanking die and bent out of the plane of the support sheet by an angle of about 90°.

* * * * *